(12) United States Patent
Volker et al.

(10) Patent No.: US 8,988,083 B2
(45) Date of Patent: Mar. 24, 2015

(54) CONDUCTIVITY SENSOR

(75) Inventors: Marco Volker, Dobeln (DE); Andreas Eberheim, Waldheim (DE); Stefan Muller, Heidenau (DE)

(73) Assignee: Endress + Hauser Conducta Gesellschaft fur Mess- und Regeltechnik mbH + Co. KG, Gerlingen (DE)

( * ) Notice: Subject to any disclaimer, the term of this patent is extended or adjusted under 35 U.S.C. 154(b) by 221 days.

(21) Appl. No.: 13/275,527

(22) Filed: Oct. 18, 2011

(65) Prior Publication Data

US 2012/0092025 A1  Apr. 19, 2012

(30) Foreign Application Priority Data

Oct. 19, 2010 (DE) .................. 10 2010 042 637

(51) Int. Cl.
*G01R 27/28* (2006.01)
*G01N 27/06* (2006.01)
*G01R 27/02* (2006.01)
*G01R 27/26* (2006.01)

(52) U.S. Cl.
CPC ............. *G01N 27/06* (2013.01); *G01R 27/02* (2013.01); *G01R 27/26* (2013.01)
USPC .............................. 324/649; 324/444; 29/622

(58) Field of Classification Search
CPC ..... G01N 27/06; G01N 27/07; G01N 27/226; G01N 2291/02416; G01R 27/2647; G01R 27/2635; G01R 31/16; G01D 11/245

USPC ...................... 257/415; 29/622; 324/444, 649
See application file for complete search history.

(56) References Cited

U.S. PATENT DOCUMENTS

| 4,118,663 | A | * | 10/1978 | Barben, II | ..................... | 324/443 |
| 4,227,151 | A | | 10/1980 | Ellis | | |
| 5,973,503 | A | | 10/1999 | Kuipers | | |
| 6,058,934 | A | * | 5/2000 | Sullivan | ........................ | 600/308 |
| 6,417,679 | B1 | * | 7/2002 | Lenz | ............................. | 324/722 |
| 7,800,284 | B2 | * | 9/2010 | Theuerkauf | ................... | 310/337 |
| 2005/0040834 | A1 | | 2/2005 | Sanchez | | |
| 2009/0174288 | A1 | * | 7/2009 | Theuerkauf | ................... | 310/337 |
| 2010/0164023 | A1 | * | 7/2010 | Knese et al. | ................. | 257/415 |
| 2011/0309848 | A1 | | 12/2011 | Eberheim | | |

FOREIGN PATENT DOCUMENTS

| DE | 8625284 U1 * | 1/1987 |
| DE | 40 40 333 A1 | 9/1991 |
| DE | 196 28 690 A1 | 1/1998 |
| DE | 10 2008 054 659 A1 | 6/2010 |
| EP | 1 089 072 B1 | 4/2001 |
| JP | 2009264954 A | 11/2009 |

* cited by examiner

*Primary Examiner* — Patrick Assouad
*Assistant Examiner* — Sean Curtis
(74) *Attorney, Agent, or Firm* — Bacon & Thomas, PLLC

(57) ABSTRACT

A conductivity sensor, comprising an electrode structure of four concentric electrodes, which are arranged on an end face of a support body. The electrodes are electrically insulated from one another. The electrodes have an equal, constant area in order to claim a space requirement as small as possible for the electrode structure.

6 Claims, 1 Drawing Sheet

CONDUCTIVITY SENSOR

TECHNICAL FIELD

The invention relates to a conductivity sensor, comprising an electrode structure of four concentric electrodes, which are arranged on an end face of a support body, wherein the electrodes are electrically insulated from one another.

BACKGROUND DISCUSSION

A conductivity sensor, which has a circularly cylindrical housing, wherein metal measuring electrodes are arranged planarly on a circular end wall of the cylindrical housing is known from EP 1089072 A2. The metal measuring electrodes form, in such a case, two voltage electrodes and two electrical current electrodes. The voltage electrodes are circularly embodied and surrounded by the two flat electrical current electrodes, which essentially extend in a semicircle. This arrangement has the disadvantage that it lacks rotational symmetry, which is objectionable due to an undefined end stop in the case of an installation in a screw lid, for example. The mounting of the electrode structure in the conductivity sensor is made difficult by such an undefined installation factor.

A measuring cell for measuring and monitoring the electrical conductivity of a liquid is known from U.S. Pat. No. 4,227,151. This measuring cell has a plurality of circularly shaped electrodes, which are mutually arranged at a distance, and electrically insulated, from one another. In such case, at least four concentric circular electrodes are arranged in or on a planar surface and isolated from one another by regions of electrically non-conducting material. The innermost of the four electrodes is hollow, in order to accommodate a temperature sensitive element. Such a hollow embodied electrode leads to sealing problems, since the described conductivity sensor is used for measuring the physical properties of a liquid.

A conductivity measured value transducer is known from EP 0386660 A1. Four concentric metal rings are placed as electrodes for the conductivity measured value transducer on the end face of a cylindrical support body of insulating material. In such case the electrodes are planar with the end face. In such case, the electrodes with a greater cross section are applied as electrical current electrodes, while the electrodes with a smaller cross section are applied as voltage electrodes. A disadvantage in this case is that this electrode structure requires a relatively large space due to the different cross sections of the electrodes.

SUMMARY OF THE INVENTION

An object of the invention is thus to provide a conductivity sensor, which reliably delivers an exact measurement result in spite of a small space requirement.

According to the invention, the object is achieved by features including that the electrodes have equal, constant areas. This has the advantage that the cross section is reduced from electrode to electrode. An outer electrode is thinner than an inner electrodes due to the greater diameter of the outer electrode. The resulting constant area leads to the fact that all electrodes have equal electrical current density, whereby parasitic voltages, which occur through polarization effects in the case of conduction through the liquid to be measured, cancel one another. Moreover, such a structure requires less space due to the electrodes becoming thinner toward the outside, so that the conductivity sensor is made spatially smaller.

Advantageously, the innermost electrode is embodied as a circle, while the electrodes, which surround the innermost electrode, are preferably embodied ring shaped. In such case, based on its full surfaced embodiment, the circular, innermost electrode can be provided with a very small diameter, in order to have the same area as the annular electrodes surrounding it. Moreover, the circular electrode is especially usable as an electrical current electrode, since it has a closed and thus robust electrode surface.

In a further development, the electrodes are embodied planarly on the end face of the support body. This is suitable, in such case, for the manufacture of the metal electrodes on the support body using a known method, such as a thick film, or a thin film, method or a similar method. Since these methods are well developed for mass production, a very cost effective manufacture of the electrode structure is possible.

In an embodiment, the electrodes are embodied three dimensionally, especially tubularly, extending from the end face of the support body, wherein the electrodes are arranged coaxially. Through such a nesting of the three dimensional electrodes, minimal space is required for forming the electrode structure.

In a variant, two tubular electrodes used to measure voltage have perforations. Such perforations are necessary in order to reliably assure electrical current flow between an outer and an inner electrode and thus the voltage measurement in the individual electrodes.

Alternatively, the two tubular electrodes used to measure the voltage are embodied lattice like. The uniform lattice shaped distribution of passageways through the tubular electrodes also leads to a reliable voltage measurement.

In another form of embodiment, the electrodes are equally spaced from one another. Such an embodiment simplifies the manufacture of the electrodes, especially in a thin, or thick, film method.

In a variant, the innermost electrode and the outermost electrode are fed an electrical current, while the two electrodes in between are connected to a voltage meter. Due to the cross sections of the individual electrodes, these are thus optimally utilized according to their designed structures for measuring, respectively, electrical current and voltage.

BRIEF DESCRIPTION OF THE DRAWINGS

The invention allows numerous forms of embodiment. One of these will now be explained in greater detail based on the appended drawing, the figures of which show as follows.

DETAILED DISCUSSION IN CONJUNCTION WITH THE DRAWINGS

Figure 1:
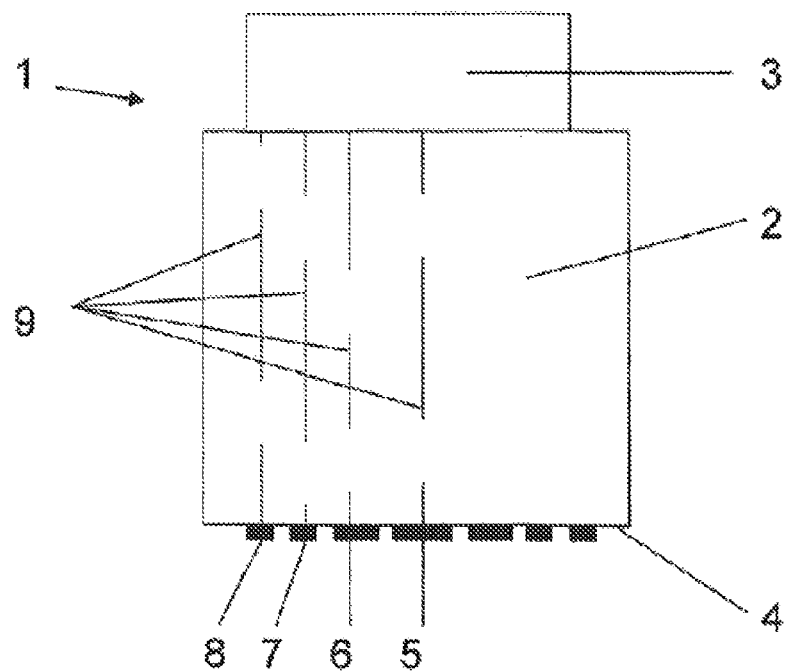
FIG. 1 is a longitudinal section through a conductivity sensor.

Equal features are provided with equal reference characters.

FIG. 1 shows a conductivity sensor 1, which is composed of an electrically insulated support body 2 and an evaluating electronics 3 connected thereto. The conductivity sensor 1 includes on the cylindrically formed support body 2 a circularly round, end face 4, on which an electrode structure of the electrodes 5, 6, 7, 8 is arranged. For measuring, each of the electrodes 5, 6, 7, 8, is connected to the evaluating electronics 3 via an electrical line 9. Since the support body 2 is composed of a nonconductive material, the electrodes 5, 6, 7, 8 are electrically insulated from one another via the support body 2 as well as also by the air forming between them.

For determining the conductivity of a liquid, the electrode structure is immersed into the liquid. The conductivity of the liquid is a measure of the amount of electrically conductive substances dissolved in the liquid, impurities for example. Prerequisite is a dissolved substance having the ability to form ions. Such conductivity sensors are preferably applied in water processing or clarification plants. All materials with mobile charge carriers such as electrons or ions have a measurable ohmic resistance.

The conductivity sensor 1, with its four electrodes 5, 6, 7, 8, described in FIG. 1 is utilized for measuring this ohmic resistance. Of these, the innermost and the outermost electrodes 5, 8 are electrical current carrying. The electrical current is fed to the electrodes 5, 8 from the evaluating electronics 3. The two other electrodes 6 and 7 lying between are used as voltage electrodes. The high impedance voltage electrodes 6, 7 sense the voltage drop within the liquid to be measured. All electrodes 5, 6, 7, 8 have the same constant area, which leads to the compensation of losses from polarization effects.

Figure 2:
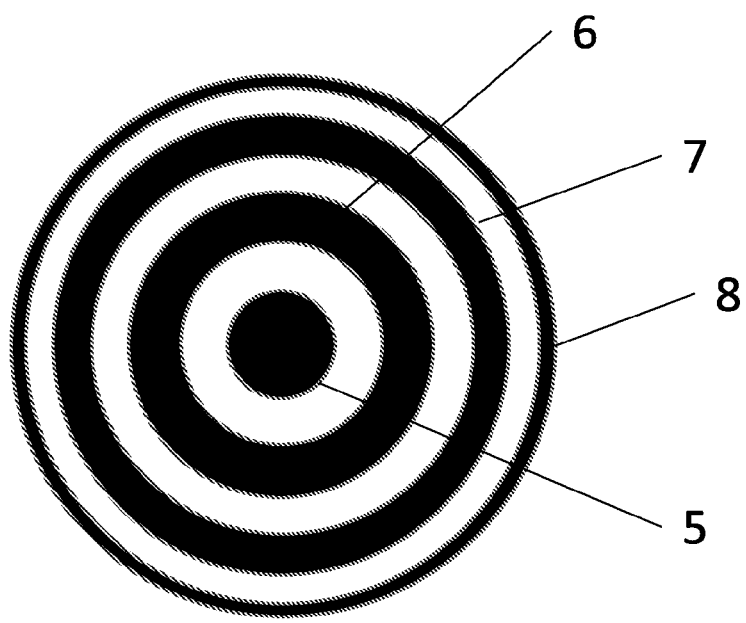
FIG. 2 is an example of an embodiment for the electrode structure of the invention.

FIG. 2 shows a plan view of the end face 4 of the support body 2, on which concentrically annular electrodes 6, 7, 8 are arranged. The electrode 5 located in the middle is circular. All four electrodes 5, 6, 7, 8 have the same constant area.

This leads to each electrode 6, 7, 8, which is arranged further from the center, having a smaller cross section than the internally lying electrodes 5, 6, 7 because of the greater diameter. Therewith polarization effects are prevented.

All disturbing processes, which occur at the interface between an electrode and a liquid to be measured, are combined under the terminology 'polarization effect'. Polarization increases with measurement current and conductivity; however, it decreases with rising measuring frequency. Moreover, the polarization effect is strongly dependent on the material of the electrodes. Thus stainless steel electrodes are suitable only for use in a lower conductivity range because of the strong polarization effect. Graphite and plated platinum are suitable as electrode materials for higher conductivity ranges. Due to the constant area of the electrodes 5, 6, 7, 8 all electrodes 5, 6, 7, 8 have the same electrical current density, whereby parasitic effects as a result of polarization effects cancel each other in the case of these annular electrodes 5, 6, 7, 8.

The electrodes 5, 6, 7, 8 illustrated in FIG. 2 form a planar, concentric arrangement; the electrodes are applied to the end face 4 of the support body 2 in a screen printing method using thick film technology. However, it is also conceivable that these are implemented using thin film technology. The distances between the electrodes 5, 6, 7, 8 are equal in such case. This enables a simpler manufacture of the electrode structure on the end face with a space requirement as small as possible.

The invention claimed is:

1. A conductivity sensor, comprising:
   a support body defining an end face; and
   an electrode structure of four concentric electrodes, which are arranged on said end face of said support body, wherein:
   said electrodes are electrically insulated from one another, and have an equal, constant area, and
   the innermost electrode is circular, while the remaining electrodes surrounding said innermost electrode are ring-shaped.

2. The conductivity sensor as claimed in claim 1, wherein:
   said electrodes are embodied planarly on said end face of said support body.

3. The conductivity sensor as claimed in claim 1, wherein:
   said electrodes are embodied three dimensionally on said end face of said support body; and
   said electrodes are arranged coaxially.

4. The conductivity sensor as claimed in claim 1, wherein:
   said electrodes are separated an equal distance from one another.

5. The conductivity sensor as claimed in claim 1, wherein:
   an electrical current is fed to the inner electrode and the outermost electrode, while the two electrodes lying between are connected to a voltage measurement.

6. The conductivity sensor as claimed in claim 3, wherein:
   said electrodes are embodied tubularly on said face end of said support body.

* * * * *